United States Patent
Locke et al.

(10) Patent No.: US 9,757,500 B2
(45) Date of Patent: *Sep. 12, 2017

(54) SYSTEMS AND METHODS FOR DELIVERING FLUID TO A WOUND THERAPY DRESSING

(71) Applicant: KCI Licensing, Inc., San Antonio, TX (US)

(72) Inventors: Christopher Brian Locke, Bournemouth (GB); Kevin W. Bendele, Fort Worth, TX (US); James A. Luckemeyer, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 191 days.

This patent is subject to a terminal disclaimer.

(21) Appl. No.: 14/705,823

(22) Filed: May 6, 2015

(65) Prior Publication Data

US 2015/0238667 A1   Aug. 27, 2015

Related U.S. Application Data

(63) Continuation of application No. 13/477,659, filed on May 22, 2012, now Pat. No. 9,050,208.

(Continued)

(51) Int. Cl.
*A61M 1/00* (2006.01)
*A61F 13/00* (2006.01)

(52) U.S. Cl.
CPC ..... *A61M 1/0058* (2013.01); *A61F 13/00068* (2013.01); *A61M 1/0023* (2013.01); *A61M 1/0025* (2014.02); *A61M 1/0031* (2013.01); *A61M 1/0035* (2014.02); *A61M 1/0037* (2013.01); *A61M 1/0084* (2013.01);
(Continued)

(58) Field of Classification Search
CPC .............. A61M 1/0023; A61M 1/0031; A61M 1/0037; A61M 1/0058; A61M 1/0062; A61M 27/00; A61F 13/00068
See application file for complete search history.

(56) References Cited

U.S. PATENT DOCUMENTS

| 1,355,846 A | 10/1920 | Rannells |
| 2,547,758 A | 4/1951 | Kelling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery, Jun. 1997.

(Continued)

*Primary Examiner* — Tatyana Zalukaeva
*Assistant Examiner* — Benjamin Klein (57) ABSTRACT

Systems and methods for delivery of fluid to a wound therapy dressing. In exemplary embodiments, a pressure sensor measures the pressure at the wound therapy dressing and restricts fluid flow to the wound therapy dressing when a predetermined pressure is achieve.

28 Claims, 6 Drawing Sheets

Related U.S. Application Data (60) Provisional application No. 61/490,880, filed on May 27, 2011.

(52) U.S. Cl.
CPC ........ *A61M 1/0088* (2013.01); *A61M 1/0092* (2014.02); *A61M 2205/3344* (2013.01)

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 9,050,208 | B2 * | 6/2015 | Locke ................ A61M 1/0084 |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2007/0032762 | A1 * | 2/2007 | Vogel .................. A61F 13/0216 604/305 |
| 2007/0118096 | A1 * | 5/2007 | Smith ................... A61B 5/445 604/541 |
| 2009/0275884 | A1 * | 11/2009 | McNulty ............ A61K 31/7088 604/35 |
| 2009/0306609 | A1 * | 12/2009 | Blott .................. A61M 1/0037 604/305 |
| 2011/0015587 | A1 | 1/2011 | Tumey et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |

(56) References Cited

FOREIGN PATENT DOCUMENTS

| WO | 99/13793 A1 | 3/1999 |
|---|---|---|
| WO | 2008100446 A2 | 8/2008 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

* cited by examiner

SYSTEMS AND METHODS FOR DELIVERING FLUID TO A WOUND THERAPY DRESSING

CROSS-REFERENCE TO RELATED APPLICATIONS

This application is a continuation of U.S. application Ser. No. 13/477,659, filed May 22, 2012, which claims the benefit of U.S. Provisional Patent Application No. 61/490,880, filed May 27, 2011, the entire contents of which are incorporated herein by reference.

BACKGROUND OF THE INVENTION

Field of the Invention

Embodiments of the invention relate to fluid (e.g., liquid) delivery to a wound therapy dressing and more particularly relate to systems and methods for automated fluid delivery to a negative pressure wound therapy dressing.

Description of the Related Art

Existing fluid delivery systems for wound therapy dressings are typically based on infusion systems. It is worth noting that with drug delivery systems, the user is responsible for determining the dosage of the fluids and would not generally use an automated system to determine the desired volume of liquid that should be delivered.

However, if one considers the art with respect to fluid delivery for wound dressings, such an approach may not be appropriate. For example, wound dressing fluid delivery systems are not delivering intravenous drugs. Furthermore, wounds are not uniform and indeed will change volume as the therapy progresses. Consequently, using techniques employed in other areas to prescribe a dose volume may result in under- or over-delivery of fluids with the commensurate problems. In existing delivery systems, fluid pressure may be monitored to determine if there is a line blockage, but it is typically not monitored to determine the pressure of the fluid at the site of delivery.

The referenced shortcomings are not intended to be exhaustive, but rather are among many that tend to impair the effectiveness of previously known techniques in fluid delivery to wound dressings; however, those mentioned here are sufficient to demonstrate that the methodologies appearing in the art have not been satisfactory and that a significant need exists for the techniques described and claimed in this disclosure. Instillation of fluid as an adjunct to negative pressure wound therapy (NPWT) is currently accomplished by asking the user to specify an instillation time (gravity feed systems) or instillation volume (active pumping systems).

Because it is difficult to judge the volume of a dressed wound, either approach can be problematic and time-consuming to arrive at the desired fill volume. A "Fill Assist" approach has also been used, which requires the user to stop metered fluid flow based on visual observation of the wound filling; whereafter, the automated system dispenses the same volume in subsequent instillation cycles.

However, even this simplified approach requires that the user be attentive to stopping the flow, and can easily lead to over-filling the wound, waste of NPWT collection canister volume, and potentially instillation fluid leakage at the dressing. It is therefore desirable that automated systems and methods be developed to allow the user to determine when the wound dressing has received the proper volume of liquid for instillation.

SUMMARY OF THE INVENTION

From the foregoing discussion, it should be apparent that a need exists for a system and method for improved delivery of fluid to a wound therapy dressing.

The method in the disclosed embodiments substantially includes the steps necessary to carry out the functions presented above with respect to the operation of the described system.

Exemplary embodiments of the present disclosure can provide automated delivery of fluid to a wound therapy dressing. Such automation not only frees a caregiver from having to be attentive to the device rather than the patient, but addresses a perceived problem in that the caregiver may have difficulty making a judgment about when the dressing is appropriately filled.

Exemplary embodiments can provide for increased efficiency in both caregiver's time and reduced waste of instillation fluids. For example, exemplary embodiments can reduce the likelihood of accidental overfilling of the dressing caused by a distracted or non-attentive user or caregiver. Such overfilling can require a time-consuming cycling of the system in order to repeat the fluid delivery feature or cause other operational issues. Further, there is no requirement for the caregiver to estimate wound volume or provide other input to the automated fill system.

Exemplary embodiments of this disclosure provide an automated fluid delivery system, improving the caregiver's ability to determine the correct fill level which in turn ensures that the pneumatic performance is not compromised by an overfill condition.

Exemplary embodiments of the present disclosure are configured for delivering fluid to a volume space, which have (prior to instillation) been evacuated to a known pressure and verified to not have leaks. Exemplary embodiments have the advantage of using the equalization of pressure which occurs as a fluid fills the dressing volume to provide an indicator of the correct fill level.

Certain embodiments include a system for delivering fluid to a negative pressure wound therapy dressing. In specific embodiments, the system comprises: a wound dressing; a negative pressure source coupled to the wound dressing; a fluid flow device in fluid communication with the wound dressing; a control device configured to control a fluid flow from the fluid flow device; and a pressure sensor coupled to the wound dressing and to the control device. In particular embodiments, the pressure sensor is configured to send a control signal to the control device and control fluid flow from the fluid flow device when pressure sensor detects a predetermined pressure at the wound dressing. Certain embodiments comprise a visual or audible indicator when the pressure sensor detects the predetermined pressure at the wound dressing. In particular embodiments, the fluid flow device can be a pump, including for example, a peristaltic pump or a centrifugal pump. In certain embodiments the fluid flow device can be a valve.

In specific embodiments, the control device is a control switch configured to turn the pump on or off. In particular embodiments, the control device is an actuator configured to change the position of the valve. In certain embodiments, the fluid flow device is a solenoid-actuated pinch valve. Particular embodiments may further comprise a reservoir coupled to the negative pressure source and in fluid communication with the fluid flow device. In specific embodiment, a fluid can flow from the reservoir to the wound dressing via a gravity feed system.

Particular embodiments may also comprise a check valve between the wound dressing and the reservoir, where the check valve is configured to restrict fluid flow to the reservoir when the reservoir is not at a negative pressure. In certain embodiments, the control device comprises a control switch configured to stop operation of the fluid flow device when the pressure sensor detects a predetermined pressure at the wound dressing. In specific embodiments, the control device comprises a solenoid valve configured to close when the pressure sensor detects a predetermined pressure at the wound dressing. In particular embodiments, the predetermined pressure is between approximately −1.0 mm Hg and 1.0 mm Hg, and in specific embodiments approximately 0.0 mm Hg.

Certain embodiments comprise a method for delivering fluid to a wound therapy dressing. In particular embodiments, the method comprises: creating a negative pressure on a wound therapy dressing; delivering fluid to the wound therapy dressing; monitoring pressure at the wound therapy dressing via a pressure sensor; and restricting fluid delivery when the pressure reaches a predetermined value. In specific embodiments, restricting the fluid delivery comprises activating a control switch to cut off a supply of energy to a pump. In particular embodiments, restricting fluid delivery comprises closing a valve between a fluid flow device and the wound therapy dressing. In certain embodiments, the valve can be a solenoid valve.

Specific embodiments further comprise deactivating the negative pressure source prior to delivering fluid to the wound therapy dressing. Certain embodiments further comprise providing fluid flow to the wound therapy dressing via a gravity feed system. Particular embodiments further comprise providing a reservoir between the negative pressure source and the wound therapy dressing. Certain embodiments can also comprise providing a check valve between the negative pressure source and the wound therapy dressing, where the check valve is configured to restrict flow from the negative pressure source to the wound therapy dressing. Specific embodiments can also comprise venting the reservoir to atmosphere after de-activating the negative pressure source and prior to activating the pump to deliver fluid to the wound therapy dressing. In particular embodiments, the predetermined pressure is between approximately −1.0 mm Hg and 1.0 mm Hg, and in specific embodiments approximately 0.0 mm Hg.

Other features and associated advantages will become apparent with reference to the following detailed description of specific embodiments in connection with the accompanying drawings.

The term "coupled" is defined as connected, although not necessarily directly, and not necessarily mechanically.

The terms "a" and "an" are defined as one or more unless this disclosure explicitly requires otherwise.

The term "substantially" and its variations are defined as being largely but not necessarily wholly what is specified as understood by one of ordinary skill in the art, and in one non-limiting embodiment "substantially" refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

The term "negative pressure" refers to an absolute pressure that is lower than the absolute atmospheric pressure at the location of use of the device. A stated level of negative pressure in a region is therefore a relative measure between the absolute atmospheric pressure and the absolute pressure in the region. A statement that the negative pressure is increasing means the pressure in the region is moving towards atmospheric pressure (i.e. the absolute pressure is increasing). Where numeric values are used, a negative sign is placed in front of the numeric pressure value to indicate the value is a negative pressure relative to atmospheric pressure.

BRIEF DESCRIPTION OF THE DRAWINGS

The following drawings form part of the present specification and are included to further demonstrate certain aspects of exemplary embodiments of the present invention.

DETAILED DESCRIPTION OF EXEMPLARY EMBODIMENTS

Various features and advantageous details are explained more fully with reference to the non-limiting embodiments that are illustrated in the accompanying drawings and detailed in the following description. Descriptions of well-known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

In the following description, numerous specific details are provided, such as examples of material selections, dimensions, etc., to provide a thorough understanding of the present embodiments. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1:
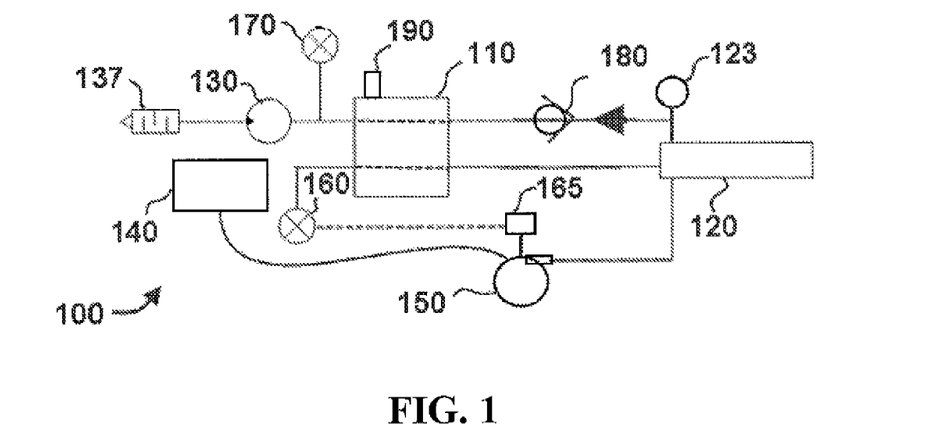
FIG. 1 is a schematic block diagram illustrating one embodiment of a system for delivering fluid to a wound therapy dressing in a first mode of operation.
Figure 2:
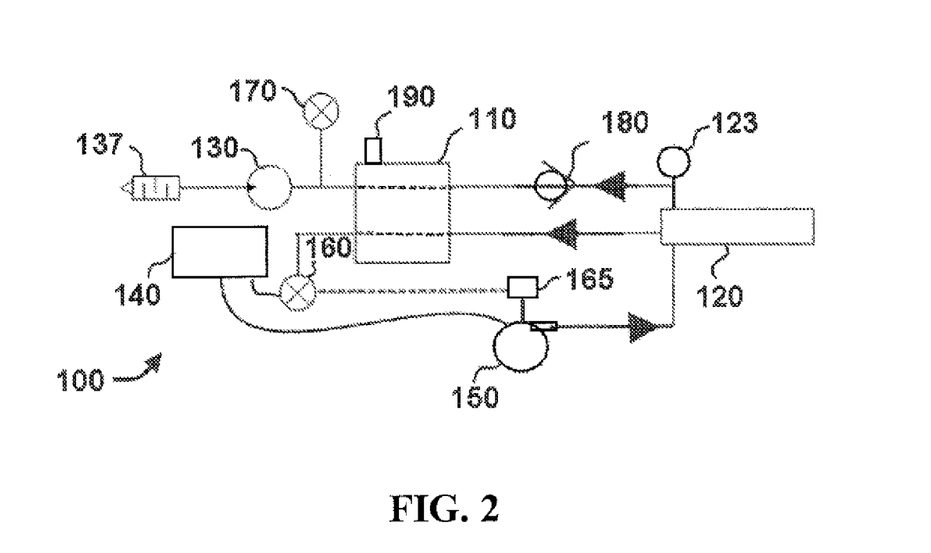
FIG. 2 is a schematic block diagram of the embodiment of FIG. 1 in a second mode of operation.
Figure 3:
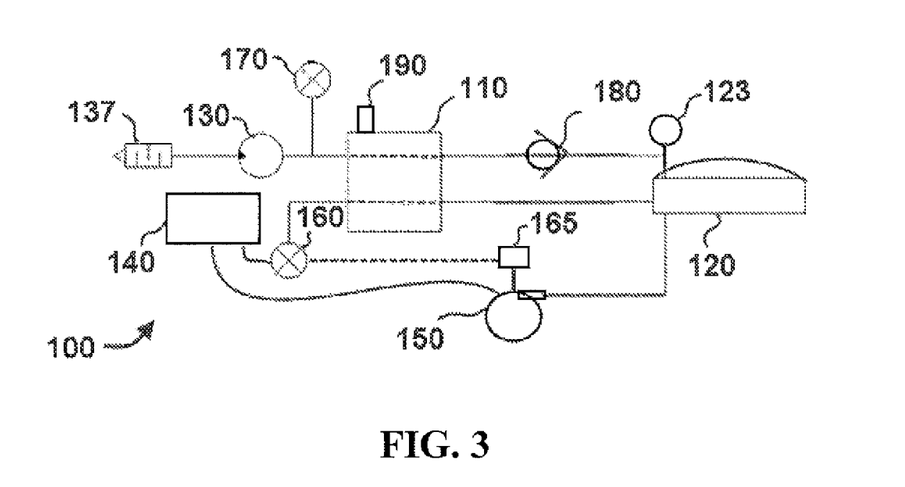
FIG. 3 is a schematic block diagram of the embodiment of FIG. 1 in a third mode of operation.

FIGS. 1-3 illustrate one embodiment of a system 100 for providing fluid delivery to a negative pressure wound therapy system. In the exemplary embodiment shown, system 100 includes a reservoir 110, a wound dressing 120, and a negative pressure source 130 coupled to reservoir 110 and wound dressing 120. In this embodiment, system 100 further comprises a fluid flow device 150 (e.g. a pump or valve, as discussed below) in fluid communication with a fluid supply reservoir 140 and wound dressing 120.

Certain embodiments may utilize a gravity fluid flow from fluid supply reservoir 140 to wound dressing 120 without utilizing a pumping device for fluid flow device 150. In such embodiments, fluid flow device 150 may be a valve (e.g., a solenoid-actuated pinch valve) configured to control the flow of fluid between fluid supply reservoir 140 and wound dressing 120. In still other embodiments, negative pressure source 130 may draw fluid into wound dressing 120 from fluid supply reservoir 140, without the aid of gravity feed or a pumping action from fluid flow device 150.

In particular exemplary embodiments, negative pressure source 130 may comprise a diaphragm vacuum pump. In certain embodiments, system 100 may also comprise a filter or muffler 137 coupled to negative pressure source 130 to reduce the operating noise of negative pressure source 130 and/or filter air exiting negative pressure source 130.

In certain exemplary embodiments, fluid flow device 150 may comprise a pump, e.g., a peristaltic, centrifugal or other suitable pump. In other exemplary embodiments, fluid flow device may comprise a gravity feed system instead of (or in conjunction with) a pump to deliver fluid to wound dressing 120. In such embodiments, a valve between the gravity feed system and wound dressing 120 can be used to restrict the fluid flow to wound dressing 120 when the predetermined pressure is reached, as explained more fully below.

In the disclosed embodiment, system 100 also comprises a vent 190 on reservoir 110, and a check valve 180 configured to allow flow in the direction from wound dressing 120 towards negative pressure source 130, and restrict fluid flow in the reverse direction. The exemplary embodiment shown in FIGS. 1-3 also comprises a pressure sensor 160 coupled to wound dressing 120, as well as a pressure sensor 170 coupled to negative pressure source 130 and wound dressing 120.

FIGS. 1-3 illustrate three modes of operation of system 100. In FIG. 1, negative pressure source 130 is activated to create a negative pressure on wound dressing 120, while fluid flow device 150 is not activated. In FIG. 2, negative pressure source 130 is not activated, but fluid flow device 150 is activated to provide a fluid flow to wound dressing 120. In FIG. 3, both negative pressure source 130 and fluid flow device 150 are not activated.

During initial operation of system 100 shown in FIG. 1, negative pressure source 130 is activated to create a negative pressure on reservoir 110 and wound dressing 120. The pressure at negative pressure source 130 and reservoir 110 and wound dressing 120 can be monitored via pressure sensor 170, as well as pressure sensor 160 (assuming normal operation without blockages in the conduit coupling the components). When the desired level of negative pressure (e.g., −125 mm Hg) is achieved, negative pressure source 130 can be deactivated and vent 190 can be opened to vent reservoir 110 to atmosphere. In certain embodiments, check valve 180 maintains the negative pressure on wound dressing 120, which can be monitored via pressure sensor 160. In particular embodiments, check valve 180 may be a duckbill type or ball-check type or flap type valve.

Fluid flow device 150 can then be activated to begin fluid delivery to wound dressing 120. In particular embodiments, fluid flow device 150 may be configured to flow approximately 100 ml/minute. As fluid is pumped from fluid flow device 150 to wound dressing 120, the pressure at wound dressing 120 (which can be monitored via pressure sensor 160) will increase. When wound dressing 120 reaches a predetermined pressure, pressure sensor 160 (which may be used to sense both positive and negative pressures) can send a control signal to control device 165 (e.g. a control switch or actuator) to restrict fluid flow from fluid flow device 150 to wound dressing 120. The increase in pressure of wound dressing 120 can be used as an indication that fluid from fluid flow device 150 has sufficiently filled wound dressing 120. By monitoring the pressure of wound dressing 120 with pressure sensor 160, system 100 can reduce the likelihood that wound dressing 120 will be overfilled. This can reduce waste of fluid and leakage of wound dressing associated with overfilling. It is understood that interface circuitry (not shown) may be utilized to generate a sufficiently strong control signal and to implement the control logic.

As previously mentioned, in certain embodiments, fluid flow device 150 may be a valve (e.g., a solenoid-actuated pinch valve) that restricts fluid flow from fluid supply reservoir 140 or a pump that is activated to provide fluid flow. The operation of fluid flow device 150 (e.g., the position of a valve or the activation/deactivation of a pump) may be automatically altered when a predetermined pressure is reached at wound dressing 120. In exemplary embodiments, the predetermined pressure of wound dressing 120 at which the operation of fluid flow device 150 is altered may be approximately 1.0 mm Hg (gauge pressure as measured by pressure indicator 160). In specific embodiments the predetermined pressure may be −10 and 10 mm Hg, including −10, −9, −8, −7, −6, −5, −4, −3, −2, −1, 0, 1, 2, 3, 4, 5, 6, 7, 8, 9 or 10 mm Hg, or any values between.

In other embodiments a user may monitor pressure sensor 160 and manually control operation of fluid flow device 150 when wound dressing 120 reaches the predetermined pressure. For example, a user may deactivate fluid flow device 150 by manipulating a control switch or restrict fluid flow from fluid flow device 150 by closing a valve.

When wound dressing 120 is sufficiently filled with fluid, the user may continue with the desired fluid instillation and vacuum therapy treatments. Exemplary embodiments can be used for each instillation cycle, which may offer advantages for wound dressings on articulated joints (e.g., knee) where the wound or dressing volume could be influenced by the patient's body position. In certain embodiments utilizing a foam dressing, the dressing volume can change over time in part due to compression-set of the foam. For example, the volume of the foam may be reduced over time as the foam is subjected to pressure. This change in volume occupied by the foam can affect the volume of fluid needed to fill wound dressing 120. Such volume changes can be accommodated by exemplary embodiments, which utilize pressure readings to indicate when the wound dressing has received a sufficient volume of liquid.

It is understood that the features shown FIGS. 1-3 and described in the accompanying discussion of the figures are merely one exemplary embodiment of the present disclosure. Other embodiments, for example, may utilize absorption layers in the wound dressing instead of, or in addition to, a reservoir.

Figure 4:
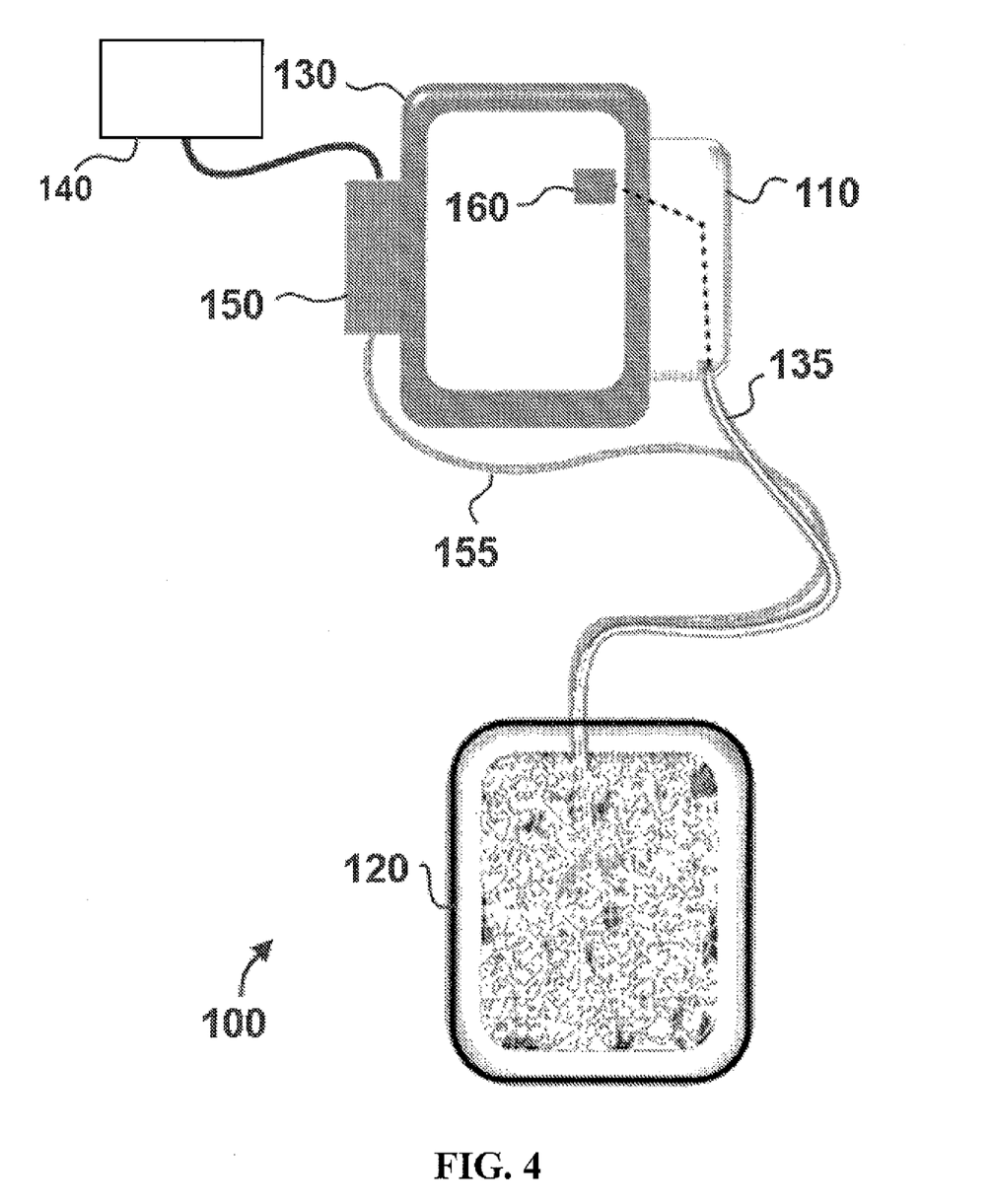
FIG. 4 is an orthogonal view illustrating the embodiment of FIG. 1 for delivering fluid to a wound therapy dressing in a first mode of operation.
Figure 5:
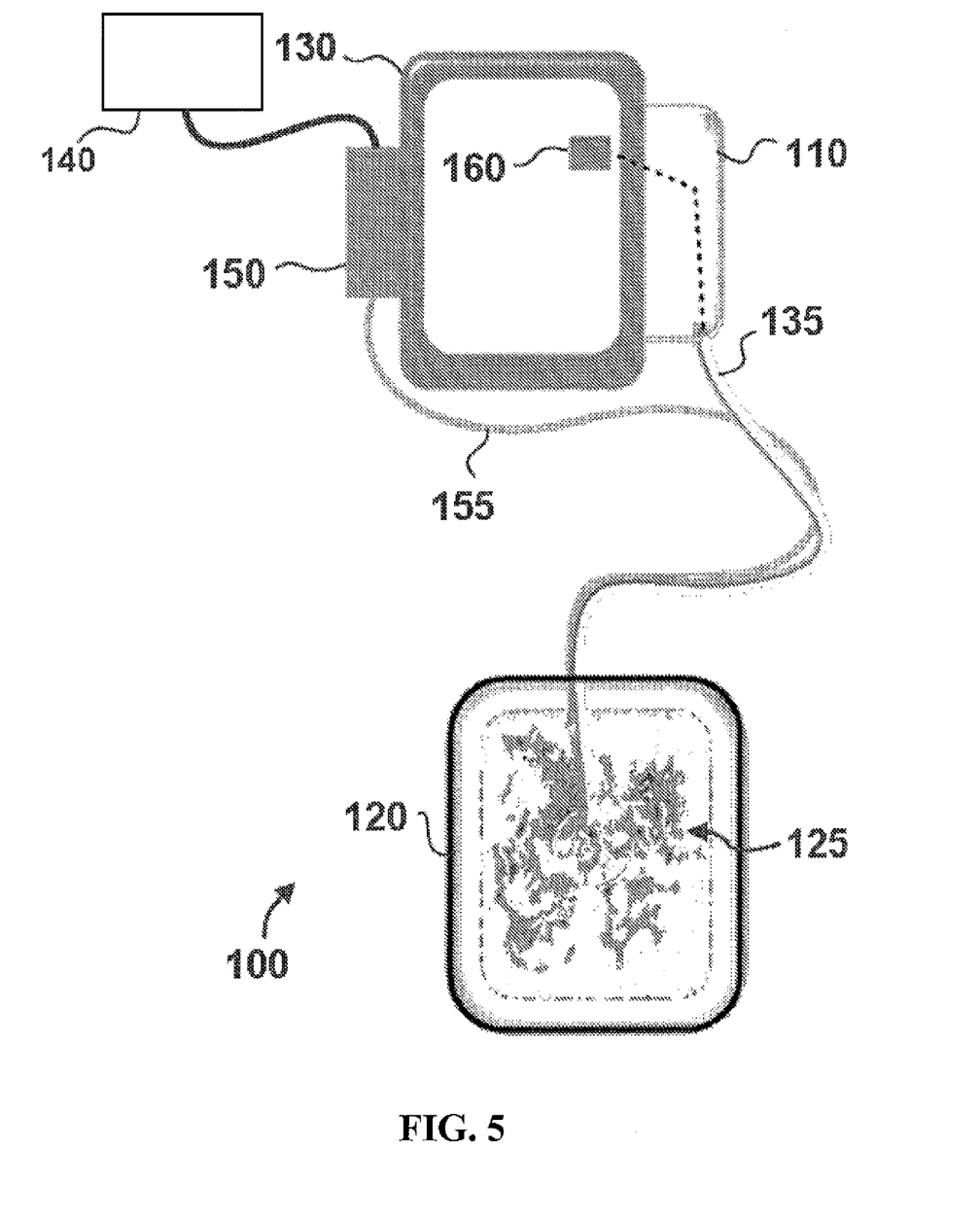
FIG. 5 is an orthogonal view illustrating the embodiment of FIG. 4 in a second mode of operation.
Figure 6:
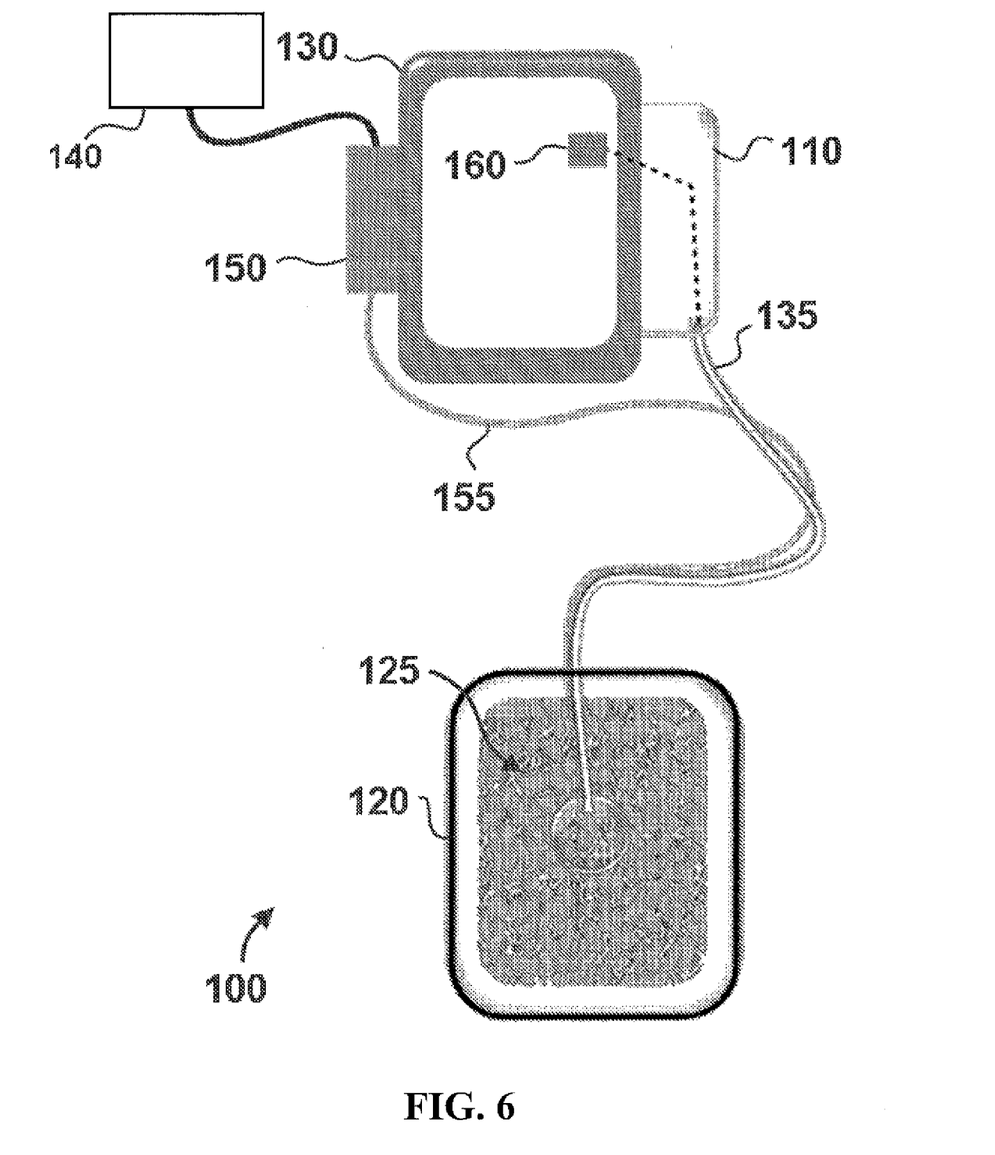
FIG. 6 is an orthogonal view illustrating the embodiment of FIG. 4 in a second mode of operation.

Referring now to FIGS. 4-6, orthogonal views of previously-described system 100 are shown in the three modes of operation illustrated in FIGS. 1-3. In FIG. 4, negative pressure source 130 is activated to create a negative pressure on reservoir 110 and wound dressing 120 (via conduit 135). In this stage of operation, there is no fluid in wound dressing 120.

As shown in FIG. 5, negative pressure source 130 is deactivated, and fluid flow device 150 is activated to begin fluid flow to wound dressing 120. As shown in FIG. 5, fluid 125 from fluid flow device 150 has begun entering wound dressing 120, via conduit 155. As fluid 125 enters wound dressing 120, the pressure measured by pressure sensor 160 increases.

Referring now to FIG. 6, a sufficient volume of fluid 125 has entered wound dressing 120 to increase the pressure to the predetermined pressure, indicating that the desired volume of fluid 125 is located in wound dressing 120. At this stage of operation, pressure sensor 160 can provide information to a control circuit to restrict the flow of fluid 125 from fluid flow device 150. As explained above, pressure sensor 160 may send a control signal to control the operation of fluid flow device 150. For example, pressure sensor 160 may send a control signal to deactivate fluid flow device 150 if it is configured as a pump. Pressure sensor 160 may also send a control signal to close a valve if fluid flow device 150 is configured as a valve.

In certain embodiments, system 100 may comprise an audible or visual pressure indicator 123 at the dressing or elsewhere in the negative pressure path (e.g., a Prevena™ dressing type available from Kinetic Concepts, Inc., San Antonio, Tex. U.S.A. has a visual indicator that retracts when the dressing is below a pressure setpoint and extends when the dressing is above the pressure setpoint) that the predetermined pressure has been reached and that wound dressing 120 contains a sufficient volume of fluid 125. At this stage, the user may proceed with the desired fluid instillation and vacuum therapy treatments.

The schematic flow chart diagrams that follow are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 7:
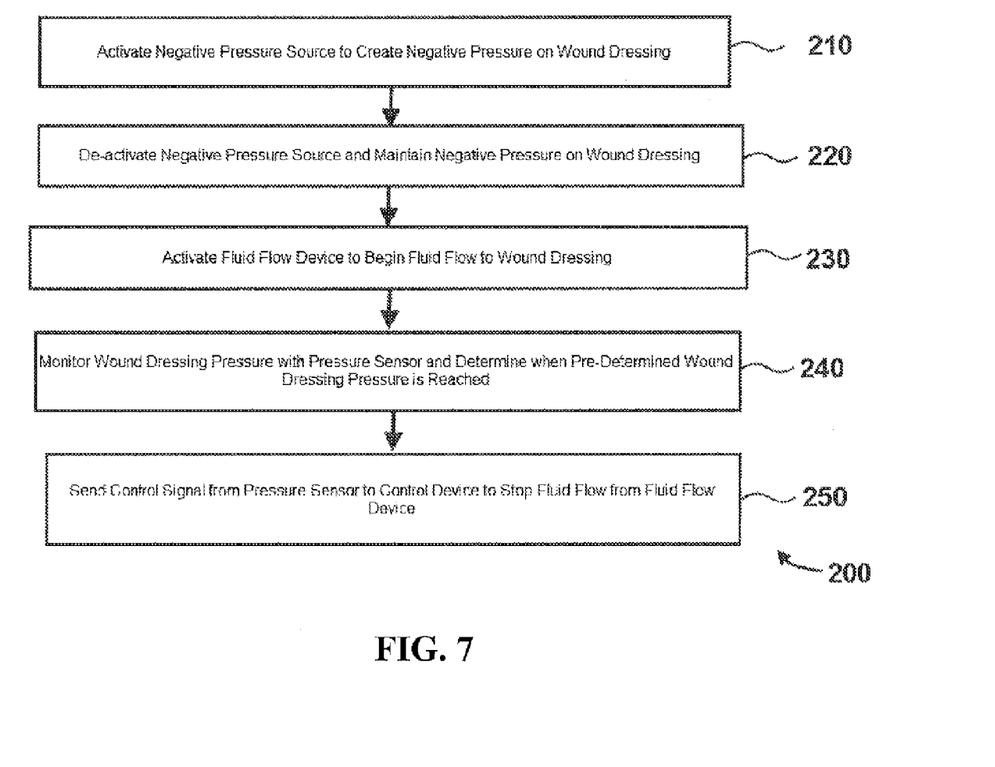
FIG. 7 is a flowchart illustrating a series of steps that can be performed in one embodiment of a method for delivering fluid to a wound therapy dressing.

Referring now to FIG. 7, a method 200 is disclosed comprising a series of steps that may be executed for the operation of an exemplary system according to this disclosure. Certain embodiments may comprise a tangible computer readable medium comprising computer readable code that, when executed by a computer, causes the computer to perform operations comprising the steps disclosed in FIG. 7.

In this exemplary embodiment, step 210 comprises activating the negative pressure source to create negative pressure on the wound dressing. Step 220 comprises de-activating the negative pressure source and maintaining negative pressure on the wound dressing. Step 230 comprises activating the fluid flow device to begin fluid flow to the wound dressing, in this embodiment. Step 240 comprises monitoring the wound dressing pressure with the pressure sensor and determining when the predetermined wound dressing pressure is reached. In this embodiment, step 250 comprises sending a control signal from the pressure sensor to the control device to stop the fluid flow from the fluid flow device.

All of the methods disclosed and claimed herein can be made and executed without undue experimentation in light of the present disclosure. While the apparatus and methods of this invention have been described in terms of preferred embodiments, it will be apparent to those of skill in the art that variations may be applied to the methods and in the steps or in the sequence of steps of the method described herein without departing from the concept, spirit and scope of the invention. In addition, modifications may be made to the disclosed apparatus, and components may be eliminated or substituted for the components described herein, where the same or similar results would be achieved. All such similar substitutes and modifications apparent to those skilled in the art are deemed to, be within the spirit, scope, and concept of the invention as defined by the appended claims.

We claim:

1. A system for delivering fluid to a wound dressing, the system comprising:
   a negative pressure source configured to evacuate the wound dressing;
   a fluid flow device in fluid communication with the wound dressing;
   a reservoir in fluid communication with the wound dressing;
   a vent configured to open the reservoir to atmosphere;
   a valve between the wound dressing and the reservoir, the valve configured to restrict fluid flow from the negative pressure source to the wound dressing;
   a pressure sensor coupled to the wound dressing and configured to send a control signal when the pressure sensor detects a predetermined pressure at the wound dressing; and
   a control device coupled to the pressure sensor, the control device configured to deliver fluid from the fluid flow device to the wound dressing until the pressure sensor sends the control signal to the control device.

2. The system of claim 1 wherein the fluid flow device is a pump.

3. The system of claim 2 wherein the control device is a control switch configured to turn the pump on or off.

4. The system of claim 1 wherein the fluid flow device is a peristaltic pump.

5. The system of claim 1 wherein the fluid flow device is a centrifugal pump.

6. The system of claim 1 wherein the fluid flow device is a second valve.

7. The system of claim 6 wherein the control device is an actuator configured to change the position of the second valve.

8. The system of claim 1 wherein the fluid flow device is a solenoid-actuated pinch valve.

9. The system of claim 1 wherein the control device comprises a control switch configured to stop operation of the fluid flow device when the pressure sensor detects the predetermined pressure at the wound dressing.

10. The system of claim 1 wherein the control device comprises a solenoid valve configured to close when the pressure sensor detects the predetermined pressure at the wound dressing.

11. The system of claim 1 wherein the predetermined pressure is between approximately −1.0 mm Hg and 1.0 mm Hg.

12. A method for delivering fluid to a wound therapy dressing, the method comprising:
providing a negative pressure source and a reservoir between the negative pressure source and the wound therapy dressing;
activating the negative pressure source to create a negative pressure on the wound therapy dressing;
restricting fluid flow to the wound therapy dressing to maintain the negative pressure on the wound therapy dressing;
delivering fluid to the wound therapy dressing;
deactivating the negative pressure source prior to delivering fluid to the wound therapy dressing;
venting the reservoir to atmosphere after deactivating the negative pressure source and prior to delivering fluid to the wound therapy dressing;
monitoring pressure at the wound therapy dressing via a pressure sensor; and
restricting fluid delivery when the pressure reaches a predetermined value.

13. The method of claim 12 wherein restricting the fluid delivery comprises activating a control switch to cut off a supply of energy to a pump.

14. The method of claim 12 wherein restricting fluid delivery comprises closing a second valve between a fluid flow device and the wound therapy dressing.

15. The method of claim 14 wherein the second valve is a solenoid valve.

16. The method of claim 12 wherein delivering fluid comprises providing fluid flow to the wound therapy dressing via a gravity feed system.

17. A system for delivering fluid to a wound dressing, the system comprising:
a negative pressure source for providing a negative pressure to the wound dressing;
a reservoir in fluid communication with the wound dressing and the negative pressure source;
a vent in fluid communication with the reservoir;
a valve between the wound dressing and the reservoir, the valve configured to restrict fluid flow toward the wound dressing when the wound dressing is at the negative pressure;
a pressure sensor in fluid communication with the wound dressing and configured to sense a predetermined pressure at the wound dressing; and
a fluid flow device configured to be activated for delivering fluid to the wound dressing when the negative pressure source is deactivated, the fluid flow device further configured to be deactivated for restricting fluid flow to the wound dressing when the wound dressing is at the predetermined pressure.

18. The system of claim 17, wherein the vent is configured to open the reservoir to atmosphere.

19. The system of claim 17, wherein the reservoir is in fluid communication with atmosphere through the vent when the negative pressure source is deactivated.

20. The system of claim 17, wherein the valve comprises a check valve.

21. The system of claim 17, wherein the valve is configured to allow fluid flow from the wound dressing to the negative pressure source.

22. The system of claim 17, wherein the valve is configured to maintain the negative pressure at the wound dressing.

23. The system of claim 17, further comprising a control device configured to deactivate the fluid flow device for restricting fluid flow to the wound dressing when the pressure sensor senses the predetermined pressure at the wound dressing.

24. The system of claim 17, further comprising a control device configured to receive a control signal from the pressure sensor to deactivate the fluid flow device when the pressure sensor senses the predetermined pressure at the wound dressing.

25. The system of claim 17, wherein the fluid flow device is a pump.

26. The system of claim 17, wherein the fluid flow device is a peristaltic pump.

27. The system of claim 17, wherein the fluid flow device is in fluid communication between a fluid supply reservoir and the wound dressing.

28. The system of claim 17, wherein the predetermined pressure is indicative of a desired volume of fluid in the wound dressing.

* * * * *